United States Patent [19]

Grijpma et al.

[11] Patent Number: 5,492,997
[45] Date of Patent: Feb. 20, 1996

[54] COPOLYMER OF LACTONE AND CARBONATE AND PROCESS FOR THE PREPARATION OF SUCH A COPOLYMER

[75] Inventors: Dirk W. Grijpma; Erik Kroeze; Atze J. Nijenhuis, all of Groningen; Albertus J. Pennings, Norg, all of Netherlands

[73] Assignee: Rijksuniversiteit te Groningen, Groningen, Netherlands

[21] Appl. No.: 256,007

[22] PCT Filed: Dec. 21, 1992

[86] PCT No.: PCT/NL92/00234

§ 371 Date: Jun. 17, 1994

§ 102(e) Date: Jun. 17, 1994

[87] PCT Pub. No.: WO93/13154

PCT Pub. Date: Jul. 8, 1993

[30] Foreign Application Priority Data

Dec. 20, 1991 [NL] Netherlands ............................ 9102148

[51] Int. Cl.⁶ ................................................. C08G 64/00

[52] U.S. Cl. ........................... 528/198; 528/196; 528/354; 528/355

[58] Field of Search ..................................... 528/196, 198, 528/354, 355

[56] References Cited

FOREIGN PATENT DOCUMENTS

| 0057360 | 8/1982 | European Pat. Off. . |
|---|---|---|
| 0427185 | 4/1992 | European Pat. Off. . |
| 0444282 | 8/1992 | European Pat. Off. . |

*Primary Examiner*—James J. Seidleck
*Assistant Examiner*—Terressa Mosley
*Attorney, Agent, or Firm*—Peter L. Michaelson; Edward M. Fink

[57] ABSTRACT

A copolymer of a lactone and a polycyclic carbonate is prepared by heating a monomer of a lactone with a polycyclic carbonate having two cyclic structures including a carbonate group at elevated temperatures less than 200 degrees Centigrade in the presence of a catalyst. The described copolymers evidence excellent mechanical properties, good resorption velocity and do not disintegrate upon degradation into materials of high crystallinity.

17 Claims, No Drawings

COPOLYMER OF LACTONE AND CARBONATE AND PROCESS FOR THE PREPARATION OF SUCH A COPOLYMER

The invention relates to a copolymer of at least one lactone and at least one cyclic carbonate.

Such a copolymer is known from U.S. Pat. No. 4,705,820, which patent specification discloses a copolymer of glycolide and trimethylene carbonate (TMC).

Such polymers and copolymers are applied, inter alia, in the medical world, where objects on the basis of these materials are implanted in the human or animal body. If the implanted material is to fulfill a (temporary) supporting function, good material-properties, such as toughness and stiffness, are required.

One way of obtaining a good toughness and stiffness is to use semi-crystalline material. Semi-crystalline material can be obtained, for instance, by the use of controlled polymerization conditions or special after-treatments, both as known from literature.

Such polymers and copolymers further are interesting mainly because the material is biodegradable. This implies that the polymer hydrolyzes and disintegrates into its constituent parts under certain biological conditions, such as for instance physiological conditions.

An implanted object based on such polymers or copolymers should not stay in the body for too long so as to avoid any tissue reactions and give the body-specific structure, which the implant was meant to support, the chance to regain its own firmness. This means that rapid degradation and resorption are required as soon as the temporary support function of the implant is no longer needed.

The drawback of copolymers with a high crystallinity is that they disintegrate into high-crystallinity, possibly needle-shaped fragments during degradation, which are resorbed only very slowly, on account of which tissue reactions may occur that are harmful to the patient.

It is the object of the invention to furnish a copolymer that possesses good mechanical properties, has a good resorption velocity and does not cause troublesome complications upon degradation.

According to the invention this is achieved in that the carbonate is polycyclic.

This renders it possible to obtain cross-linked copolymers. The mechanical properties of objects based on these copolymers are significantly better than those of objects on the basis of non-cross-linked copolymers. The material is tough—in particular the tensile strength is higher—, impact resistant, less crystalline than non-cross-linked copolymer and it is biodegradable.

The degradation velocity under physiological conditions of the copolymer according to the invention is higher than that of non-cross-linked polymers. Because of the lower crystallinity, the fragments formed upon degradation are less harmful. Mostly they are relatively small and thus cause fewer problems in the body. The crystallinity and the crystal dimensions can be derived, inter alia, from the thermal properties.

An added advantage of the copolymer according to the invention is that it may start swelling in a certain environment, so that in principle it is suitable for use as a so-called drug-release system. To this end the object involved is made to swell in a swelling medium, a drug is introduced into the swollen material, and subsequently the object is reduced to its normal proportions by removing the swelling medium or by reducing the swelling-promoting properties of the medium, for instance by adding an amount of non-swelling medium. After this, the object may be implanted.

Cross-linking of copolymers of lactones is disclosed in U.S. Pat. No. 4,379,138, in which an amount of lactone is copolymerized with a polycyclic dilactone. U.S. Pat. No. 4,379,138 does not state that this is possible also with a polycyclic carbonate.

Copolymers of lactones and cyclic carbonates are disclosed in GB-A-2,033,411, but the monocyclic carbonates described therein cannot be cross-linked.

The use of polycyclic carbonates for polyester cross-linking is disclosed in GB-A-1,228,490 which, however, does not disclose the possibility of cross-linking a copolymer on the basis of lactones. The polyesters in GB-A-1,228,490 are polyesters obtained by esterification reactions between dicarboxylic acids and diols.

Lactones and cyclic carbonates both are cyclic esters.

Cyclic esters have a schematic structural formula according to FIG. (I):

Cyclic esters are understood to include cyclic diesters with a schematic structural formula according to FIG. (II):

Lactones have a schematic structure according to formula (III):

Cyclic carbonates have a schematic structure according to formula (IV):

Examples of lactones are lactide, glycolide, ε-caprolactone, dioxanone, 1,4-dioxane-2,3-dione, beta-propiolactone, tetramethyl glycolide, beta-butyrolactone, gamma-butyrolactone or pivalolactone.

Preferably, the lactone is a lactide, such as L-lactide, D-lactide or D,L-lactide or combinations of these, and more preferably L-lactide. Lactides are preferred to glycolides since glycolides cause faster hydrolysis of the (co)polymer and may give rise to a tissue reaction in the body, to a greater extent than lactide might.

Lactide is understood to be a di-lactide having a structural formula according to FIG. (V):

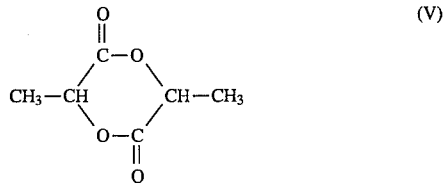

A lactide is generally formed by ring formation by esterification of 2 lactic acids.

Polycyclic carbonates are molecules with at least two cyclic structures that contain a carbonate group. Preferably, the number of cyclic structures that contain a carbonate group is approximately two per molecule.

Polycyclic carbonates are disclosed in, for instance, GB-A-1,228,490 and EP-A-0,057,360, both of which are hereby included as references.

Preferably, the polycyclic carbonate is a carbonate as described in EP-A-0,057,360, and more preferably it is a molecule on the basis of pentaerythritol, which is similar to trimethylene carbonate (TMC). An example of such a molecule is 2,4,7,9,tetraoxa-spiro[5,5]undecanedione[3,8], which will further be referred to as spiro-bis-dimethylene carbonate [Spiro-bis-DMC]. Such a monomer has a structure according to formula (VI):

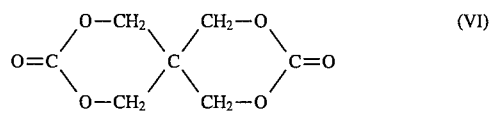

(VI)

Polyfunctional carbonates can be produced by a process as disclosed in EP-A-0,057,360, which is hereby included as a reference.

Spiro-bis-DMC can be obtained, for instance, through reaction of pentaerythritol and diethyl carbonate.

Further, it is possible to incorporate all possible other monomers into the copolymer. Preferably, monomers are incorporated that can react via ring opening polymerization. These monomers may, for instance, be chosen from the group formed by cyclic ethers, cyclic carbonates and cyclic anhydrides.

In addition, the following substances may be copolymerized:
alpha-hydroxy butyric acid,
alpha-hydroxy isobutyric acid,
alpha-hydroxy valeric acid,
alpha-hydroxy isovaleric acid,
alpha-hydroxy caproic acid,
alpha-hydroxy isocaproic acid,
alpha-hydroxy alpha-ethyl butyric acid,
alpha-hydroxy beta-methyl valeric acid,
alpha-hydroxy heptanoic acid,
alpha-hydroxy octanoic acid,
alpha-hydroxy decanoic acid,
alpha-hydroxy stearic acid or combinations hereof.
or the intermolecular cyclic esters of these monomers.

A further list can be found in GB-A-1,604,177, which is hereby included as a reference.

The copolymer can be synthesized in ways that are known to one skilled in the art and that are described in a general sense, for instance, in EP-A-0,108,365, which is hereby included as a reference.

The cyclic carbonate and the lactone can, for instance, be reacted during 240 hours in the melt at 110° C. with tin octoate as catalyst.

The temperature preferably used depends on, among other things, the polymerization method and the catalyst concentration. The temperature chosen is generally above the melting point of the monomer and below 200° C. Preferably, a temperature between 100° and 150° C. is chosen.

The polymerization time chosen may be between a few minutes and a few weeks. In general, the polymerization time chosen is between 30 minutes and 2 weeks, and preferably between 20 and 200 hours. More preferably, the polymerization time is 60–150 hours. The required or preferred polymerization time depends on the temperature chosen and the catalyst concentration.

The reaction can take place in the melt, in solution, in emulsion, suspension or in any other manner. Preferably, the reaction takes place in the melt.

As catalyst use may be made of, for instance, tin octoate, antimony trifluoride, metallic zinc (powder), dibutyltin oxide and/or tin oxalate. More catalysts are disclosed in EP-A-0,098,394, which is hereby included in the description as a reference. Further, use may be made of all esterification catalysts known to one skilled in the art as well as anionic and cationic catalysts.

The monomer/catalyst ratio is preferably between 1000 and 300,000, and more preferably between 5000 and 30,000.

The reaction can take place under a vacuum, in, for instance, sealed ampoules, or under an inert atmosphere, such as nitrogen.

The copolymer can subsequently be purified or it can be used in as-copolymerized condition. The material as obtained after polymerization, so without, for instance, an additional purification or remelting step, is called as-polymerized material. Preferably, use is made of as-polymerized material.

The copolymer generally contains 0.01 to 50 mol % of units derived from polycyclic carbonate and 50 to 99.99 mol % of units derived from lactones.

Preferably, the copolymer contains 0.01 to 5% polycyclic carbonate, and more preferably it contains 0.01 to 3 mol %, and most preferably 0.1 to 1%.

A further advantage of such a polyfunctional carbonate, and notably of Spiro-bis-DMC, is that it disintegrates into non-toxic products upon hydrolytical degradation. In the case of Spiro-bis-DMC the disintegration products are pentaerythritol and $CO_2$.

Objects can be made from the copolymer by heating, drawing, milling, turning and/or optionally all kinds of other operations. Milling and turning, for instance, do not or hardly change the as-polymerized structure.

It is further possible to produce objects by having the polymerization reaction take place in a mould having a shape that corresponds to the desired shape. Use can be made, for instance, of the Reaction Injection Moulding (RIM) technique.

Such copolymers can also be drawn, so that considerable further improvement of certain mechanical properties is possible. Drawing can be effected to at least 10×.

The copolymers according to the invention have surgical applications, for instance as medical implants. It is possible to manufacture objects having an impact strength in excess of 50 $kJ/m_2$ and a tensile strength of at least 70 MPa. Such objects have not yet been described in the literature.

Preferably, objects according to the invention are applied in medical implants that are subjected to a high mechanical load, such as in compression screws, bone plates or screws for securing bone plates.

The invention will be elucidated on the basis of the following examples, without being limited thereto.

The impact strength, I.S., was measured using unnotched Dynstat test specimens according to DIN 53453 using a 1 J hammer.

The melting temperature Tm, the melting heat ΔH, and the glass transition temperature Tg were measured by means of a DCS measurement using a calibrated Perkin Elmer DSC-7 with a scanning speed of 10° C. $min^{-1}$ on test specimens weighing about 10 mg. The Tg was measured in a second measurement cycle, after cooling from the melt.

The tensile strength a and the elongation at break ε were determined by means of a stress-strain curve, which was measured using an Instron 4301 Tensile Tester (Limited High Wycombe) with a Load Cell of 5000N and a crosshead speed of 10 mm.$min^{-1}$ on samples measuring 4×6×50 mm.

EXAMPLE I

Synthesis of Spiro-bis-DMC

An amount of 12.5 g pentaerythritol was powdered and introduced into a 3-necked flask, which contained 75.9 g diethylene carbonate (DEC) and 0.1 wt. % potassium carbonate as catalyst.

The flask was heated to 120° C. in an oil bath, ethanol being distilled off and pentaerythritol being dissolved. After a predetermined amount of ethanol had been distilled off, the excess DEC was distilled off by raising the temperature to 150° C.

The polycondensate formed was dissolved in dichloromethane (DCM) and washed with 2 n HCl and with water. After drying with $Na_2SO_4$ a depolymerization catalyst (0.1 wt. % tin octoate) was added. The DCM was removed by evaporation and the DEC still present was removed by distillation at 150° C. and 10 mm Hg.

The product was ground to increase the depolymerization area and at 240° C. and 0.003 mm Hg Spiro-bis-DMC was sublimated from the ground product.

The Spiro-bis-DMC was washed with DCM. FTIR, NMR and elementare analysis proved that it was indeed Spiro-bis-DMC that had been obtained.

EXAMPLE II

Polymerization of Lactones and Polycyclic Carbonate

An amount of a) L-lactide b) D,L-lactide c) ε-caprolactone and d) lactide mixture with trimethylene carbonate (TMC) was reacted in an ampoule with varying amounts of Spiro-bis-DMC according to Example I. The lactides had been supplied by Purac Biochem, the Netherlands, the ε-caprolactone had been supplied by Janssen, Belgium, and the TMC had been obtained by a synthesis starting from propane diol and diethylene carbonate. The reaction took place during seven days under a vacuum at 110° C., unless stated otherwise. Also present was $10^{-4}$ moles of tin octoate catalyst/mole of monomer. The molar ratios and a description of the appearance of the resulting products are presented in Table 1.

TABLE 1

| Lactones and Spiro-bis-DMC | | | |
|---|---|---|---|
| cyclic esters | Spiro-bis-DMC (mol %) | T (°C.) | Product appearance |
| a) L-lactide | 2 | 150 | glassy |
| L-lactide | 4.3 | 110 | semi-crystalline |
| L-lactide | 1.7 | 110 | semi-crystalline |
| b) D,L-lactide | 2.0 | 130 | glassy |
| c) ε-caprolactone | 1.9 | 110 | tough semi-crystalline |
| d) L-lactide/TMC 50/50 | 1.0 | 110 | tough low-crystallinity |
| L-lactide/TMC 98/2 | 1.0 | 110 | semi-crystalline |

All copolymers formed were insoluble in chloroform and had a gel percentage of at least 95%. It can be concluded that Spiro-bis-DMC is an adequate cross-linking agent for these cyclic esters.

Mechanical comparison of experiments IIa, b, c and d proves that experiments IIa give the best results.

In vitro tests showed that the resorbability of the copolymers is good.

The tensile strengths of experiment a were 70, 68 and 70 mPa, while the impact strengths were around 15 $kJ/m^2$.

A DSC measurement proved that the crystallinity of the copolymers was considerably lower than that of the poly-L-lactide, viz. 40 and 70%, respectively, for 1.7 and 0 mol % Spiro-bis-DMC, respectively. The values of the mechanical properties are very high for copolymers with such a low crystallinity.

Comparative Experiment A

Polymerization Without Polycyclic Carbonate

The process of Example IIa was repeated without Spiro-bis-DMC. The crystallinity of the product was higher than that of any of other product of Example II. The tensile strength was around 58 MPa, while the impact strength was about 9 $kJ/m^2$.

EXAMPLE III

Lactide With Different Percentages of Spiro-bis-DMC

The process of Example IIa was applied using different amounts of Spiro-bis-DMC. The composition was found to reach a gelling point already at 0.06 mol % Spiro-bis-DMC, which indicates that Spiro-bis-DMC is a good cross-linking agent.

Cross-linked polylactide is further found to a have a very high draw ratio. This means that such a cross-linked poly-1-lactide copolymer was still quite capable of being drawn. A bar consisting of lactide with 36 mol % Spiro-bis-DMC with a length of 6 cm and a diameter of 0.84 mm could be drawn to 11× at 200° C.

This test was repeated two times. The resulting bar diameters were 0.253, 0.254 and 0.256 mm, while the tensile strengths at room temperature were 671, 630 and 688 MPa, respectively.

This test was repeated once more with a bar containing 0.10 mol % Spiro-bis-DMC. This bar could be drawn to 14× and had an initial diameter of 0.86 mm, while the diameters after drawing were 0.25, 0.25 and 0.23 mm. The tensile strengths were 753, 759 and 806 MPa, respectively.

Improvement of the mechanical properties is known, for instance from EP-0,321,176, but the mechanical properties achieved according to said publication are not as good as the results obtained with a product according to the invention.

The melting point and the melting heat of the various copolymers drop rapidly with an increasing molar percentage of Spiro-bis-DMC, up to about 2%. Above this value, the melting point and the melting heat no longer drop rapidly.

The tensile strength increases with an increasing molar percentage of Spiro-bis-DMC, up to a value of about 70 MPa at 2%.

The impact strength of the copolymer has a sharp maximum of more than 45 $kJ/m^2$ between 0.1 and 1 mol %, in particular between 0.2 and 0.3 mol %.

We claim:

1. Copolymer of a lactone and a polycyclic carbonate having at least two ring structures, each of which includes a carbonate group.

2. Copolymer according to claim 1, characterized in that the lactone is a lactide.

3. Copolymer according to claim 1, characterized in that the polycyclic carbonate is a molecule with approximately two cyclic structures that contain a carbonate group.

4. Copolymer according to claim 3, characterized in that the polycyclic carbonate is spiro-bis-dimethylene carbonate.

5. Copolymer according to claim 1, characterized in that the copolymer further contains units derived from cyclic esters, cyclic carbonates and/or cyclic anhydrides.

6. Copolymer according to claim 1, characterized in that the copolymer consists of 0.01 to 50 mol % of units derived from polycyclic carbonate and 50 to 99.99 mol % of units derived from lactones.

7. Copolymer according to claim 6, characterized in that the copolymer consists of 0.01 to 5 mol % of units derived from polycyclic carbonate and 97 to 99.9 mol % of units derived from lactones.

8. Copolymer according to claim 7, characterized in that the copolymer consist of 0.1 to 1.0 mol % of units derived from polycyclic carbonate.

9. A copolymer obtained by copolymerization of at least one lactone and at least one cyclic carbonate, characterized in that the carbonate is polycyclic having at least two ring structures, each of which includes a carbonate group and in that the copolymer has a tensile strength of at least 630 MPa.

10. Process for the polymerization of a copolymer of a lactone and a polycyclic carbonate which comprises heating a monomer of a lactone and a polycyclic carbonate having two cyclic structures that include a carbonate group at a temperature less than 200° C. for a time period ranging from 30 minutes to two weeks in the presence of a catalyst at a monomer to catalyst ratio ranging from 1000:1 to 300,000:1.

11. Process in accordance with claim 10 wherein the temperature ranges from 100°–150° C., the time period ranges from 60–150 hours, the monomer to catalyst ration ranges from 5,000:1 to 30,000:1 and the lactone is a lactide.

12. Process in accordance with claim 10 wherein the catalyst is tin octoate.

13. Process in accordance with claim 10 wherein the reaction is effected in a vacuum.

14. Process in accordance with claim 10 wherein the reaction is effected in an inert atmosphere.

15. Process in accordance with claim 14 wherein the inert atmosphere is nitrogen.

16. Copolymer prepared in accordance with claim 10 having an impact strength greater than 50 kJ/$m_2$ and a tensile strength of at least 70 MPa.

17. Copolymer prepared in accordance with claim 10 which is drawn to at least ten times its original size.

* * * * *